United States Patent
Toler et al.

(10) Patent No.: US 8,569,381 B2
(45) Date of Patent: Oct. 29, 2013

(54) COMBINATION THERAPY FOR THE MANAGEMENT OF HYPERTENSION

(75) Inventors: Steven M. Toler, Winston-Salem, NC (US); David A. Hosford, Durham, NC (US)

(73) Assignee: Targacept, Inc., Winston-Salem, NC (US)

( * ) Notice: Subject to any disclaimer, the term of this patent is extended or adjusted under 35 U.S.C. 154(b) by 0 days.

(21) Appl. No.: 13/262,882

(22) PCT Filed: May 22, 2009

(86) PCT No.: PCT/US2009/044937
§ 371 (c)(1),
(2), (4) Date: Dec. 20, 2011

(87) PCT Pub. No.: WO2009/143403
PCT Pub. Date: Nov. 26, 2009

(65) Prior Publication Data
US 2012/0115917 A1   May 10, 2012

Related U.S. Application Data

(60) Provisional application No. 61/055,771, filed on May 23, 2008.

(51) Int. Cl.
*A61K 31/13* (2006.01)

(52) U.S. Cl.
USPC ............ 514/661; 514/381; 514/563; 514/616; 514/660

(58) Field of Classification Search
USPC .................................. 514/563, 616, 660, 661
See application file for complete search history.

(56) References Cited

U.S. PATENT DOCUMENTS

| 4,922,901 | A  |   | 5/1990  | Brooks et al. |
| 5,986,142 | A  |   | 11/1999 | Magni et al. |
| 6,071,939 | A  | * | 6/2000  | Gaviraghi et al. ............ 514/356 |
| 6,541,479 | B1 | * | 4/2003  | Mehanna et al. ........ 514/255.01 |
| 6,635,648 | B2 | * | 10/2003 | Adams et al. ............ 514/252.17 |
| 6,951,860 | B2 | * | 10/2005 | Mehanna et al. ........ 514/252.12 |
| 7,101,916 | B2 |   | 9/2006  | Shytle et al. |
| 2008/0119557 | A1 |   | 5/2008 | Webb et al. |

FOREIGN PATENT DOCUMENTS

| WO | WO 00-35279   | 6/2000 |
| WO | WO 2004-080446 | 9/2004 |
| WO | WO 2006-086456 | 8/2006 |

OTHER PUBLICATIONS

Brown, N. J., et al, "Angiotensin-Converting Enzyme Inhibitors," *Circulation*, 97: 1411-1420 (1998).
Kaplan, N. M., "Angiostensin II receptor Antagonists in the Treatment of Hypertension," *Am Fam. Physician*, 60: 1185-90 (1999).
Kassler-Taub, K., et al., "Comparative Efficacy of Two Angiotensin II Receptor Antagonists, Irbesartan and Losartan, in Mild-to-Moderate Hypertension," *Amer. J. Hypertension*, 2(4): 445-453 (1998).
Israili, Z. H., "Clinical Pharmokinetics of Angiotensin II (AT1) Receptor Blockers in Hypertension," *J. Human Hypertension*, 14(1): S73-S86 (2000).
Oparil, S., et al., "Hypertension," *Disease-A-Month*, 35(3): 138-232 (1989).

* cited by examiner

*Primary Examiner* — My-Chau T Tran
(74) *Attorney, Agent, or Firm* — Amy H. Fix

(57) ABSTRACT

The present invention includes a combination comprising: a) mecamylamine; and b) an ACE inhibitor, an AT2 receptor inhibitor, a renin inhibitor, or a combination thereof.

10 Claims, No Drawings

COMBINATION THERAPY FOR THE MANAGEMENT OF HYPERTENSION

CROSS REFERENCE TO RELATED APPLICATION

This application claims priority to PCT Application Number PCT/US2009/044937, with an International Filing Date of May 22, 2009, which claims priority to U.S. Provisional Patent Application Ser. No. 61/055,771, filed May 23, 2008, each of which is herein incorporated by reference in its entirety.

BACKGROUND OF THE INVENTION

Recently, a US National Committee has defined prehypertension individuals as those with persistent blood pressure between 120/80 mm Hg and 139/89 mm Hg. The prehypertension designation identifies people with higher risk of developing hypertension, along with a higher risk for cardiovascular disease. According to the American Heart Association, some 65 million American adults have hypertension and an additional 59 million adults have prehypertension. Hypertension and prehypertension together thus affect more than half of all adults in the US. Many of these individuals are not being treated for their essential hypertension and most of those under treatment with antihypertensive drugs do not reduce blood pressure to the desired level of 115/75 mmHg throughout a 24 hour day. Therefore, there is an unmet need for better antihypertensive treatments.

Normal blood pressure is considered 120/80 mm Hg, but some recent data indicate that 115/75 mm Hg or below is the desired norm. Essential or primary hypertension is defined as a chronic elevation of blood pressure of 140/90 mm Hg or above. Although hypertension seldom produces early symptoms, untreated essential hypertension extending over many years damages the heart and the blood vessels in and between the major organs resulting in increasing risks for aneurysms, arthrosclerosis, heart disease, retinopathy, strokes, and kidney damage.

The environmental and genetic risk factors for hypertension have been extensively studied. The controllable risk factors include: inactivity; excessive alcohol intake; high sodium or saturated fat diet; low potassium, magnesium, or calcium diet; excess weight or obesity; smoking or other CNS stimulants; and high stress. With the growth of fast food restaurants, overeating, decline of aerobic exercise, and hectic lifestyles, the environmental risk factors for hypertension have been increasing in the developed world. The genetic and uncontrollable risk factors for hypertension include: age, race, sex, and family history of diabetes or hypertension. Because the hypertension risk rises greatly after 50 years of age, essential hypertension is expected to increase significantly as the baby boomers reach retirement age. The increasing obesity and diabetes found in the US also raises the risks of hypertension.

The mechanisms underlying essential hypertension are not completely understood, as essential hypertension arises from unidentified causes. Cardiac output increases early in the development of hypertension and then drops as total peripheral resistance of the blood vessels rises. There are at least three theories to explain this rise in peripheral resistance: (1) the inadequate reduction of sodium by the kidneys of some individuals leads to excess water retention; (2) an overactive renin-angiotension system leads to vasoconstriction of blood vessels; and/or (3) an overactive sympathetic nervous system leads to chronic stress.

The treatment of prehypertension or mild hypertension starts with changes in lifestyle to reduce the controllable causes of hypertension such as lack of exercise, smoking, obesity, and poor diet. For those unable to control their hypertension via lifestyle changes, antihypertensive drugs are typically prescribed. Many types of antihypertensive medications are available: angiotensin-converting enzyme inhibitors, angiotensin II receptor blockers, diuretics, beta blockers, alpha-blockers, and calcium channel blockers. Which of these drug classes works best for the individual patient is often determined by trial and error. Moreover, doctors often prescribe the use of several classes of antihypertensive drugs simultaneously, as several drugs from different classes are often offer safety and efficacy advantages over higher doses of a single drug class in reaching the desired blood pressure goal.

Refractory or resistant hypertension is somewhat less common than other forms of hypertension. Definitions vary, but hypertension is usually considered refractory if blood pressure cannot be reduced below target levels in patients who are compliant with an optimal drug regimen. In patients with isolated systolic hypertension (ISH), refractoriness has been traditionally defined as a failure of multiple antihypertensive drugs to reduce systolic blood pressure to below 160 mm Hg. As noted above, recent observations strongly indicate that the target level for systolic blood pressure should be no higher than 140 mm Hg.

When blood pressure goals are not attained with standard antihypertensive drug therapy, the first steps are to determine whether the patient does have refractory hypertension and to consider some possible etiologies. The factors include environmental factors; whether the patient adhering to the prescribed regimen; whether pseudoresistance is present; whether drug interactions or adverse reactions may be at fault; whether the patient has a secondary form of hypertension such as renovascular hypertension; whether pressor mechanisms may be responsible for elevating the arterial blood pressure despite antihypertensive drug therapy; and other similar considerations.

When mecamylamine, sold under the tradename Inversine®, was in common use from 1954 to 1960, there were few options to manage blood pressure. When mecamylamine was administered by itself, it initially lowered blood pressure and also decreased renal perfusion. Renal juxtaglomerular (JG) cells responded (due to perceived hypovolemia) by activating the renin-angiotensin axis to restore blood volume and resulting in increased blood pressure. Consequently, clinicians would raise the dose of mecamylamine to counteract this effect. As the dose of mecamylamine was raised, the renin-angiotensin axis was further augmented until, at some point, following continued increasing doses, mecamylamine became poorly tolerated and less effective. At this point concentrations of mecamylamine were well above the EC50 for efficacy and circulating angiotensin 2 and aldosterone concentrations were very high. Twenty to twenty-five years later mecamylamine was no longer used, and ACE inhibitors, which block activation of the renin-angiotensin axis, entered the market.

In treating hypertension with ACE inhibitors or AT2 antagonists alone, the sympathetic system is only partially blocked, often leading to treatment-refractory hypertension. With mecamylamine alone, the renin-angiotensin pathway is activated also commonly producing refractory hypertension. Improved therapies for hypertension are desirable.

SUMMARY OF THE INVENTION

The present invention includes a combination comprising: a) mecamylamine; and b) an ACE inhibitor, an AT2 receptor inhibitor, a renin inhibitor, or a combination thereof. In one embodiment, the combination is a unitary pharmaceutical composition.

The present invention is believed to provide a synergistic drug interaction. As such, one aspect of the present invention includes a combination that provides for administration of a decreased therapeutically effective amount of each component as compared to the therapeutically effective amount of each component as individually administered.

Another aspect of the present invention includes a method of treating or inhibiting to onset of hypertension or refractory hypertension comprising the administration of: a) at least one form of mecamylamine; and b) at least one ACE inhibitor, AT2 receptor inhibitor, a renin inhibitor, or a combination thereof.

Another aspect of the present invention includes a method for reducing blood pressure in angiotensin-induced hypertension comprising the administration of: a) at least one form of mecamylamine; and b) at least one ACE inhibitor, AT2 receptor inhibitor, a renin inhibitor, or a combination thereof.

Another aspect of the present invention includes a method to reduce one or more of cardiac hypertrophy or fibrosis comprising the administration of: a) at least one form of mecamylamine; and b) at least one ACE inhibitor, AT2 receptor inhibitor, a renin inhibitor, or a combination thereof.

In some embodiments, the methods include prolonged control of blood pressure at sustained dosage levels.

Another aspect of the present invention includes a dosing regimen for the treatment of hypertension or refractory hypertension comprising: a) administering at least one form of mecamylamine; and b) administering at least one ACE inhibitor, AT2 receptor inhibitor, a renin inhibitor, or a combination thereof. In one embodiment, the at least one form of mecamylamine and the at least one ACE inhibitor, AT2 receptor inhibitor, a renin inhibitor, or a combination thereof, is administered sequentially or concomitantly. In one embodiment, the at least one form of mecamylamine and the at least one ACE inhibitor, AT2 receptor inhibitor a renin inhibitor, or a combination thereof, is administered in a unitary dosage form.

In one embodiment, the at least one form of mecamylamine and the at least one ACE inhibitor. AT2 receptor inhibitor, a renin inhibitor, or a combination thereof, are each administered in a separate dosage form.

In another aspect, the present invention includes a method of diagnosing refractory hypertension by determining a subject's response upon administration of at least one form of mecamylamine and at least one ACE inhibitor, AT2 receptor inhibitor, a renin inhibitor, or a combination thereof.

In another aspect, the present invention includes use of a) at least one form of mecamylamine; and b) at least one ACE inhibitor, AT2 receptor inhibitor, a renin inhibitor, or a combination thereof, in the preparation of a medicament for treating or inhibiting the onset of hypertension or refractory hypertension.

In another aspect, the present invention includes at least one form of mecamylamine in combination with at least one ACE inhibitor, AT2 receptor inhibitor, a renin inhibitor, or a combination thereof for use in treating or inhibiting the onset of hypertension or refractory hypertension.

In some embodiments, the aspects of the invention include prolonged control of blood pressure at sustained dosage levels.

In some embodiments of the aspects of the invention, the mecamylamine is exo-S-mecamylamine.

In some embodiments of the aspects of the invention, the AT2 receptor inhibitor is losartan.

The scope of the present invention includes all combinations of aspects and embodiments.

DESCRIPTION OF THE INVENTION

With the combination of mecamylamine and an ACE inhibitor or AT2 inhibitor, both the renal medulla and the renin-angiotensin pathways are deactivated. Thus, the compensatory routes, so-called "escape routes," are eliminated. Accordingly, blood pressure will decrease.

If mecamylamine is administered in low, tolerated doses, preferably 20 mg/day or lower comprised of one or more doses, in combination with an ACE inhibitor, an AT2 antagonist, a renin inhibitor, or some combination thereof, then reasonably well-tolerated declines in blood pressure should occur.

Preferably, the dose of mecamylamine should not need to be titrated up because the escape mechanisms will be cut off. As one example, the ACE inhibitors will block activation of the renin-angiotensin axis produced by administration of mecamylamine alone.

The combinations of the present invention can provide a superior result compared to either drug administered alone. The combinations of the present invention are believed useful in the treatment, prevention, or diagnosis of a variety of cardiovascular diseases, including cardiovascular disorders such as ischemic heart disease, hypertension, and refractory hypertension. Further examples include, but are not limited to, myocardial infarction and angina pectoris, including unstable angina pectoris.

The present invention includes a combination comprising one or more form of mecamylamine together with: (a) a calcium channel blocker; (b) an ACE inhibitor; (c) an angiotensin receptor blocker; (d) a renin inhibitor; (e) a diuretic, or (f) a combination of (a)-(e).

Mecamylamine

Unless otherwise stated herein, the term "mecamylamine" means mecamylamine, its stereoisomers together as the racemic mixture and as purified separate enantiomers, analogs, the free base, and/or salts thereof. Mecamylamine can be obtained according to the methods and processes described in U.S. Pat. No. 5,986,142, incorporated herein by reference for its teaching regarding method of producing mecamylamine. Purified exo-S-mecamylamine and exo-R-mecamylamine can be obtained according to methods discussed in U.S. Pat. No. 7,101,916, and references cited therein, also incorporated herein by reference for their teaching regarding the production of purified mecamylamine enantiomers.

Preferably, the present invention includes the administration of substantially pure S-mecamylamine. The S isomer is believed to be the more potent of the isomers at mitigating mean arterial pressure increases during sympathetic nerve stimulation.

ACE Inhibitors

ACE inhibitors useful according to the present invention include those taught in Brown, N. J. and D. E. Vaughan, Circulation, 97:1411-1420 (1998), herein incorporated by reference. ACE inhibitors useful according to the present invention include, but are not limited to, benazepril, captopril, ceronapril, enalapril, fosinopril, imidapril, lisinopril, moexipril, quinapril, ramipril, trandolapril, perindopril, and zofenopril. This list is not intended to be limiting, and other compounds known in the art as ACE inhibitors may also be used.

AT2 Inhibitors

AT2 receptor inhibitors useful according to the present invention include azilsartan, candesartan, losartan, irbesartan, eprosartan, olmesartan, tasosartan, telmisartan, valsartan, and zolarsartan. Below are representative estimated starting dosages and dosing ranges for selected AT2 inhibitors: andesartan: starting dose 16 mg once daily; dosing range 8 to 32 mg once daily rbesartan: starting dose 150 mg once daily; dosing range 150 to 300 mg once daily losartan: starting dose 50 mg once daily; dosing range 25 to 100 mg once daily telmisartan: starting dose 40 mg once daily; dosing range 20 to 80 mg once daily valsartan: starting dose 80 mg once daily; dosing range 80 to 320 mg once daily
Source: Kaplan, N. M., *Am Fam Physician* 60:1185-90 (1999), herein incorporated by reference with regard to such dosages and ranges.

Renin Antagonists/Inhibitors

Renin inhibitors useful according to the present invention include those taught in US Published Application, Publication No. 2008/0119557 A1, incorporated herein by reference for its teaching of renin inhibitors and method of obtaining such compounds. A preferred compound is aliskiren.

In addition to the aforementioned compounds, renin inhibitors useful according to the present invention include, but are not limited to, ditekiren, enalkiren, remikiren, terlakiren, and zankiren.

Other Therapeutic Compounds

In an embodiment of the present invention and as will be appreciated by those skilled in the art, the compounds of the present invention may be administered in combination with still further therapeutic compounds.

One example of a further therapeutic agent includes calcium channel blockers, namely compounds which work by blocking voltage-sensitive calcium channels in the heart and in the blood vessels. Calcium levels do not increase as much in the cells when stimulated, leading to less contraction. This decreases total peripheral resistance by dilating the blood vessels, and decreases cardiac output by lowering the force of contraction. Because resistance and output drop, so does blood pressure. With lowered blood pressure, the heart does not have to work as hard; this can ease problems with cardiomyopathy and coronary disease. Unlike with beta-blockers, the heart is still responsive to sympathetic nervous system stimulation, so blood pressure can be maintained more effectively. Calcium channel blockers useful in the present invention include dihydropyridine calcium channel blockers including amlodipine, felodipine, nicardipine, nifedipine, nimodipine, nisoldipine, nitrendipine, lacidipine, and lercanidipine; phenylalkylamine calcium channel blockers including verapamil and gallopamil; benzothiazepine calcium channel blockers including diltiazem; and other calcium channel blockers such as menthol.

As further examples, the combination of the present invention may be further combined with one or more anti-hyperlipidemic agents; anti-dyslipidemic agents; plasma HDL-raising agents; anti-hypercholesterolemic agents, including, but not limited to, cholesterol-uptake inhibitors; cholesterol biosynthesis inhibitors, e.g., HMG-CoA reductase inhibitors (also referred to as statins, such as lovastatin, simvastatin, pravastatin, fluvastatin, rosuvastatin, pitavastatin, and atorvastatin); HMG-CoA synthase inhibitors; squalene epoxidase inhibitors or squalene synthetase inhibitors (also known as squalene synthase inhibitors); acyl-coenzyme A cholesterol acyltransferase (ACAT) inhibitors, including, but not limited to, melinamide; probucol; nicotinic acid and the salts thereof; niacinamide; cholesterol absorption inhibitors, including, but not limited to, P-sitosterol or ezetimibe; bile acid sequestrant anion exchange resins, including, but not limited to cholestyramine, colestipol, colesevelam or dialkylaminoalkyl derivatives of a cross-linked dextran; LDL receptor inducers; fibrates, including, but not limited to, clofibrate, bezafibrate, fenofibrate and gemfibrozil; vitamin B6 (also known as pyridoxine) and the pharmaceutically acceptable salts thereof, such as the HCl salt; vitamin B12 (also known as cyanocobalamin); vitamin B3 (also known as nicotinic acid and niacinamide, supra); anti-oxidant vitamins, including, but not limited to, vitamin C and E and betacarotene; platelet aggregation inhibitors, including, but not limited to, fibrinogen receptor antagonists, i.e., glycoprotein IIb/IIIa fibrinogen receptor antagonists; hormones, including but not limited to, estrogen; insulin; ion exchange resins; omega-3 oils; benfluorex; ethyl icosapentate; and amlodipine; appetite-suppressing agents or anti-obesity agents including, but not limited to, insulin sensitizers, protein tyrosine phosphatase-1B (PTP-1B) inhibitors, dipeptidyl peptidase IV (DPP-IV) inhibitors, insulin or insulin mimetics, sequestrants, nicotinyl alcohol, nicotinic acid, PPARα agonists, PPARγ agonists including, but not limited to thiazolidinediones, including but not limited to rosiglitazone, troglitazone and pioglitazone; PPARα/γ dual agonists, inhibitors of cholesterol absorption, acyl CoA: cholesterol acyltransferase inhibitors, anti-oxidants, anti-obesity compounds, neuropeptide Y5 inhibitors, β3 adrenergic receptor agonists, ileal bile acid transporter inhibitors, anti-inflammatories, including NSAIDs and COX-2 selective inhibitors; insulin; sulfonylureas, including but not limited to chlorpropamide, glipizide, glyburide, and glimepiride; biguanides, including but not limited to metformin; alpha-glucosidase inhibitors, including, but not limited to, acarbose and meglitol; cannabinoid antagonists, including, but not limited to rimonabant; camptothecin and camptothecin derivatives, D-phenylalanine derivatives; meglitinides; diuretics including, but not limited to, methyclothiazide, hydroflumethiazide, metolazone, chlorothiazide, methyclothiazide, hydrochlorothiazide, quinethazone, chlorthalidone, trichlormethiazide, bendroflumethiazide, polythiazide, hydroflumethiazide, spironolactone, triamterene, amiloride, bumetanide, torsemide, ethacrynic acid, furosemide; beta-blockers including, but not limited to acebutolol, atenolol, betaxolol, bisoprolol, carteolol, metoprolol, nadolol, pindolol, propranolol, and timolol; vasodilators including, but not limited to, nitric oxide, hydralazine, and prostacyclin; alpha blockers including, but not limited to, doxazosin, prazosin and terazosin; alpha 2 agonists including, but not limited to clonidine and guanfacine; curcumin, gugulipid, garlic, vitamin E, soy, soluble fiber, fish oil, green tea, carnitine, chromium, coenzyme Q10, anti-oxidant vitamins, grape seed extract, pantothine, red yeast rice, and royal jelly; NNR ligands (such as varenicline), antioxidants (such as free radical scavenging agents), antibacterial agents (such as penicillin antibiotics), antiviral agents (such as nucleoside analogs, like zidovudine and acyclovir), anticoagulants (such as warfarin), anti-inflammatory agents (such as NSAIDs), anti-pyretics, analgesics, anesthetics (such as used in surgery), acetylcholinesterase inhibitors (such as donepezil and galantamine), antipsychotics (such as haloperidol, clozapine, olanzapine, and quetiapine), immuno-suppressants (such as cyclosporin and methotrexate), neuroprotective agents, steroids (such as steroid hormones), corticosteroids (such as dexamethasone, predisone, and hydrocortisone), vitamins, minerals, nutraceuticals, anti-depressants (such as imipramine, fluoxetine, paroxetine, escitalopram, sertraline, venlafaxine, and duloxetine), anxiolytics (such as alprazolam and buspirone), anti-convulsants (such as phenytoin and gabapentin), vasodilators (such as prazosin and sildenafil), mood stabilizers (such as valproate and aripiprazole), anti-cancer drugs (such as anti-proliferatives), antihypertensive agents (such as atenolol, clonidine, amlopidine, verapamil, and olmesartan), laxatives, stool softeners, diuretics (such as furosemide), anti-spasmotics (such as dicyclomine), anti-dyskinetic agents, and anti-ulcer medications (such as esomeprazole).

Pharmaceutical Compositions

The pharmaceutical compositions of the present invention incorporate at least one form of mecamylamine and at least one ACE inhibitor, AT2 receptor inhibitor, renin inhibitor, or a combination thereof to treat and prevent various conditions and disorders, including hypertension and refractory hypertension.

The present invention provides pharmaceutical compositions that include effective amounts of compounds, or a salt or solvate thereof, along with one or more pharmaceutically acceptable carriers, diluents, or excipients. The carrier(s), diluent(s), or excipient(s) must be acceptable, in the sense of being compatible with the other ingredients of the formulation and not deleterious to the recipient of the pharmaceutical composition.

In accordance with another aspect of the invention there is also provided a process for the preparation of a pharmaceutical formulation including admixing one or more of the active ingredient(s), including a salt, solvate, or prodrug thereof, with one or more pharmaceutically acceptable carriers, diluents, or excipients.

The manner in which the compounds are administered can vary. The compositions are preferably administered orally, for example, in liquid form within a solvent such as an aqueous or non-aqueous liquid, or within a solid carrier. Preferred compositions for oral administration include pills, tablets, capsules, caplets, syrups, and solutions, including hard gelatin capsules and time-release capsules. Compositions may be formulated in unit dose form, or in multiple or subunit doses. Preferred compositions are in liquid or semisolid form.

Compositions including a liquid pharmaceutically inert carrier such as water or other pharmaceutically compatible liquids or semisolids may be used. The use of such liquids and semisolids is well known to those of skill in the art.

The compositions can also be administered via injection, namely, intravenously, intramuscularly, subcutaneously, intraperitoneally, intraarterially, intrathecally, and intracerebroventricularly. Intravenous administration is a preferred method of injection. Suitable carriers for injection are well known to those of skill in the art, and include 5% dextrose solutions, saline, and phosphate buffered saline. The compounds can also be administered as an infusion or injection, such as, as a suspension or as an emulsion in a pharmaceutically acceptable liquid or mixture of liquids.

The formulations may also be administered using other means, for example, rectal administration. Formulations useful for rectal administration, such as suppositories, are well known to those of skill in the art. The compounds can also be administered by inhalation, including, in the form of an aerosol either nasally or using delivery articles of the type set forth in U.S. Pat. No. 4,922,901 to Brooks et al., the disclosure of which relating to such compositions and methods is incorporated herein; topically, such as, in lotion form; transdermally, such as, using a transdermal patch, using technology that is commercially available from Novartis and Alza Corporation; by powder injection; or by buccal, sublingual, or intranasal absorption.

Although it is possible to administer the compounds in the form of a bulk active chemical, it is preferred to present each compound in the form of a pharmaceutical composition or formulation for efficient and effective administration.

Exemplary methods for administering such compounds will be apparent to the skilled artisan. The usefulness of these formulations may depend on the particular composition used and the particular subject receiving the treatment. For example, the compositions can be administered in the form of a tablet, a hard gelatin capsule or as a time release capsule. These formulations may contain a liquid carrier that may be oily, aqueous, emulsified or contain certain solvents suitable to the mode of administration.

The administration of the pharmaceutical compositions described herein can be intermittent, or at a gradual, continuous, constant, or controlled rate to a warm-blooded animal, for example, a mammal such as a mouse, rat, cat, rabbit, dog, pig, cow, or monkey; but advantageously is administered to a human being. In addition, the time of day and the number of times per day that the pharmaceutical composition is administered can vary.

The appropriate dose of the compound is that amount effective to prevent occurrence of the symptoms of the disorder or to treat some symptoms of the disorder from which the patient suffers. By "effective amount", "therapeutic amount," or "effective dose" is meant that amount sufficient to elicit the desired pharmacological or therapeutic effects, thus resulting in effective prevention or treatment of the disorder.

As noted herein, prevention of the disorder may be manifested by delaying the onset of the symptoms of the disorder and treatment of the disorder may be manifested by a decrease in the symptoms associated with the disorder or an amelioration of the reoccurrence of the symptoms of the disorder.

The effective dose can vary, depending upon factors such as the condition of the patient, the severity of the symptoms of the disorder, and the manner in which the pharmaceutical composition is administered. The effective dose of compounds will of course differ from patient to patient and is within the skill of an attending physician. Typically, to be administered in an effective dose, compounds require administering in an amount of less than 5 mg/kg of patient weight. Often, the compounds may be administered in an amount from less than about 1 mg/kg patient weight to less than about 100 µg/kg of patient weight, and occasionally between about 10 µg/kg to less than 100 µg/kg of patient weight. The foregoing effective doses typically represent that amount administered as a single dose, or as one or more doses administered over a 24 hours period. For human patients, the effective dose of the compounds may require administering the compound in an amount of at least about 1, but not more than about 1000, and often not more than about 500 mg/24 hr/patient.

For mecamylamine, dosage can be from about 0.1 mg/day to about 300 mg/day. In particular embodiments, mecamylamine dosage is from about 0.5 mg/day to about 100 mg/day. In other embodiments, mecamylamine dosage can be from about 2 mg/day to about 30 mg/day. In a preferred embodiment, the mecamylamine dosage is about 10 mg/day. The foregoing effective doses typically represent that amount administered as a single dose, or as one or more doses administered over a 24 hours period. In other embodiments, mecamylamine is administered at from about 0.3 µg/kg to about 250 µg/kg of patient weight. Mecamylamine can also be administered at from about 1.5 µg/kg to about 50 µg/kg of patient weight. Preferably, mecamylamine can also be administered at about 15 µg/kg of patient weight.

The phrase "combination therapy" includes "co-therapy" or "concomitant therapy." Such phrases are intended to embrace administration of each agent in a sequential manner in a regimen that will provide beneficial effects of the drug combination, and is intended as well to embrace co-administration of these agents in a substantially simultaneous manner, such as by oral ingestion of a single dosage form having a fixed ratio of these active agents or ingestion of multiple, separate capsules for each agent. A fixed dose combination suitable for oral ingestion would be in the form of a tablet, capsule, elixir, or other pharmaceutically acceptable oral dosage form. "Combination therapy" also includes simultaneous or sequential administration by intravenous, intramuscular, or other parenteral routes into the body, including direct absorption through mucous membrane tissues, as found in the sinus passages. Sequential administration also includes drug combination where the individual agents may be administered at different times and/or by different routes but which act in combination to provide a beneficial effect.

A preferred combination therapy will consist essentially of two or more active agents. The active agents will be used in combination in a weight ratio range. A preferred range of one agent to the one or more other agents depends ultimately on the selection of the particular agent.

Thus, the present invention encompasses combination therapy. The combination therapy comprises administering to the subject a therapeutically or prophylactically effective amount of one active compound of the present invention and one or more other active compound(s). As noted, such a combination of pharmaceutically active agents may be administered together or separately and, when administered separately, administration may occur simultaneously or sequentially, in any order. The amounts of the compounds or agents and the relative timings of administration will be selected in order to achieve the desired therapeutic effect. The administration in combination of a compound of the formulae of the present invention including salts or solvates thereof with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time. The compounds of the present invention may be used in the treatment of a variety of disorders and conditions and, as such, the compounds of the present invention may be used in combination with a variety of other suitable therapeutic agents useful in the treatment or prophylaxis of those disorders or conditions.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

EXAMPLES

Example 1

Effect of Exo-S-mecamylamine on Ang II-Induced Hypertension

The following experiments are conducted to determine whether exo-S-mecamylamine [at doses of 0.3 and 3.0 mg/kg/day (free base equivalent)] reduces blood pressure in Ang II-induced hypertension in Sprague-Dawley rats (Ang II-24 µg/kg/h) and alters circulating angiotensin peptides [Ang II and Ang-(1-7)], aldosterone, and catecholamines (epinephrine and norepinephrine); to determine whether treatment with exo-S-mecamylamine reduces cardiac hypertrophy and fibrosis in Ang II-infused Sprague-Dawley rats; and to determine whether treatment with exo-S-mecamylamine alters cardiac components of the renin-angiotensin system including enzymes and proteins involved in the production of angiotensin peptides (angiotensinogen, renin, angiotensin-converting enzyme, angiotensin-converting enzyme 2, and neprelysin), angiotensin peptide receptors (AT1, AT2, AT(1-7)) and cardiac angiotensin peptides [Ang II and Ang-(1-7)].

Male Sprague-Dawley rats (6 weeks of age) are obtained and trained for two weeks for the measurement of blood pressure using the tail-cuff method (as described below). Rats are implanted with Alzet osmotic minipumps (Model 2006, Durect Corporation, for the subcutaneous delivery of 0.15 µL/h for 42 days), containing either saline or Ang II (at a dose of 24 µg/kg/h). After two weeks of treatment with Ang II, additional minipumps containing either saline or exo-S-mecamylamine, at a dose of either 0.3 mg/kg/h or 3.0 mg/kg/h, are implanted, as described in the table below. Pumps are implanted on the back of the rats between the shoulder blades and the hip for the subcutaneous delivery of the peptides, while the rats are anesthetized with isofluorane (1.5 to 2%). During treatment, blood pressure is measured weekly (for 4 weeks). The groups of animals (n=7 per group) will include: (9 weeks in life)

| Group | Treatment | Ang II (µg/kg/h) | exo-S-mecamylamine (mg/kg/day) | n |
|---|---|---|---|---|
| 1 | Saline | — | — | 7 |
| 2 | Ang II | 24 | — | 7 |
| 3 | exo-S-mecamylamine | — | 0.3 | 7 |
| 4 | Ang II/exo-S-mecamylamine | 24 | 0.3 | 7 |
| 5 | exo-S-mecamylamine | | 3 | 7 |
| 6 | Ang II/exo-S-mecamylamine | 24 | 3 | 7 |

Example 2

Effect of Co-Administration of Exo-S-Mecamylamine with the Angiotensin Receptor Blocker (ARB) Losartan The following experiments are conducted to identify a dose of the Ang II receptor blocker (ARB, aka AT2 receptor inhibitor) losartan which partially reverses in the increase in blood pressure by infusion of Ang II (at a dose of 24 µg/kg/h); and to determine whether the combination of a suboptimal dose of losartan with exo-S-mecamylamine (at a dose to be determined based upon Phase I data) more effectively reduces blood pressure and end to organ damage to the heart compared to treatment with either compound alone.

A dose of the Ang II receptor blocker losartan which partially reverses the Ang II-infused increase in blood pressure (at a concentration of 24 µg/kg/h of Ang II, administered via osmotic minipump) is determined in a short, run-in experiment using 3 doses of losartan (0.1, 1.0, and 10 mg/kg/day, in the drinking water, 3 rats per dose). Male Sprague-Dawley rats (6 weeks of age) are obtained and trained for two weeks for the measurement of blood pressure using the tail-cuff method. Rats are treated with Ang II (24 µg/kg/h, via implanted osmotic minipump) for two weeks and blood pressure is monitored twice per week. After 2 weeks, rats are treated with one of three doses of losartan (either 0.1, 1.0 or 10 mg/kg/day, administered in the drinking water and adjusted daily for body weight). Blood pressure is measured twice weekly for an additional 4 weeks. A concentration of losartan that partially reduces blood pressure is chosen (9 weeks in life).

Male Sprague-Dawley rats (6 weeks of age) are obtained and trained for two weeks for the measurement of blood pressure using the tail-cuff method. Rats are implanted with Alzet osmotic minipumps (Model 2006, Durect Corporation, for the delivery of 0.15 μL/h for 42 days), containing Ang II at a dose of 24 μg/kg/h. After two weeks of treatment with Ang II, rats are treated with losartan in their drinking water, at the concentration determined in the above experiment, to the groups indicated in the table below. Rats are also implanted with osmotic minipumps, containing either saline or exo-S-mecamylamine, at the dose determined from Example I, as indicated in the table below. Treatment continues for 4 weeks, at which time the rats are sacrificed as described below (9 weeks in life). During treatment, blood pressure is measured weekly. The sets of animals (n=7 per group) includes:

TABLE 1

| Group | Treatment | Ang II (μg/kg/h) | Losartan (TBD) | exo-S-mecamylamine (mg/kg/day) | n |
|---|---|---|---|---|---|
| 1 | Ang II | 24 | — | — | 7 |
| 2 | Ang II/losartan | 24 | TBD | — | 7 |
| 3 | Ang II/exo-S-mecamylamine | 24 | — | TBD | 7 |
| 4 | Ang II/exo-S-mecamylamine/losartan | 24 | TBD | TBD | 7 |

Rats are decapitated at the end of six weeks (Phase I—6 week treatment with Ang II, 4 week treatment with exo-S-mecamylamine; Phase II—6 week treatment with Ang II, 4 week treatment with losartan ±exo-S-mecamylamine) and trunk blood is collected for the measurement of angiotensin peptides, catecholamines, and aldosterone, as well as exo-S-mecamylamine, in a blood sample provided to them from each rat. The heart is rinsed with saline and the ventricles are separated from the atria and weighed. The heart is cut in cross-section and a slice is quick frozen and stored at −80° C. for isolation of mRNA and cardiac angiotensin peptides. The remainder of the ventricles are fixed in formalin (4%), for immunohistochemistry/immunocytochemistry. Brain sections (the cortex, cerebellum, hypothalamus, and medulla oblongata, the kidneys, and the thoracic aorta are also harvested and processed, for future experiments (e.g., to measure end organ damage to the brain, kidneys, or vasculature). Each of these tissues is divided in half and rinsed with saline; one half is quick frozen and stored at −80° C. for mRNA or protein isolation and the other section is fixed in formalin for immunocytochemistry.

Immunohistochemistry/Immunocytochemistry—A cross-sectional slice from the center of each heart is fixed overnight in 4% formalin followed by a 48 h incubation in 70% ethanol. Each slice is paraffin embedded. The embedded heart tissue is cut into five micron thick sections and stained with Hemotoxylin & Eosin (H&E) to determine morphology and measure myocyte size. Fibrosis and collagen deposition is measured in sections stained with Picrosirius Red and normalized to either total area (for interstitial fibrosis) or vessel area (for perivascular fibrosis).

Angiotensin Peptide Measurement—Blood is collected into tubes containing inhibitors to prevent peptide degradation. Ang II and Ang-(1-7) in the serum and heart are measured by radioimmunoassay.

Reverse Transcriptase (RT) Real-time Polymerase Chain Reaction (PCR)—Total RNA is isolated from the left ventricle, using TRIzol according to the manufacturer's direction, to assess angiotensinogen, renin, angiotensin-converting enzyme, angiotensin-converting enzyme 1, neprilysin, the AT1 receptor, the AT2 receptor and the AT(1-7) receptor mas. The RNA concentration and integrity are assessed using an Agilent 2100 Bioanalyzer with an RNA 6000 nano Lab-Chip. Approximately 1 μg of total RNA is reverse transcribed using avian myeloblastosis virus reverse transcriptase (RT) in a 20 μL mixture containing deoxyribonucleotides, random hexamers and RNase inhibitor in RT buffer. Heating the RT reaction product at 95° C. terminates the reaction. For real-time polymerase chain reaction (PCR), 2 μL of the resultant cDNA is added to TaqMan Universal PCR Master Mix (Applied Biosystems, Foster City, Calif.) with an ACE2 primer/probe set (forward primer 5'-CCCAGAGAACAGTGGAC-CAAAA-3'; reverse primer 5'-GCTCCACCACACCAACGAT-3'; and probe 5'-FAM-CTCCCGCTTCATCTCC-3') or primer/probe sets from Applied Biosystems, Foster City, Calif. Amplification is performed on an ABI 7000 Sequence Detection System. The mixtures are heated at 50° C. for 2 min, at 95° C. for 10 min followed by 40 cycles at 95° C. for 15 sec and 60° C. for 1 min. All reactions are performed in triplicate and 18S ribosomal RNA, amplified using the TaqMan Ribosomal RNA Control Kit (Applied Biosystems), serves as an internal control. The results are quantified as Ct values, where Ct is defined as the threshold cycle of PCR at which amplified product is first detected, and expressed as the ratio of target/control (Relative Gene Expression).

Indirect blood pressure—Systolic blood pressures are determined weekly utilizing a computer automated tail-cuff analysis system (Hatteras SC-1000, Hatteras Instruments, Cary, N.C.). Rats are acclimated to the system for 2 to 4 sessions and blood pressure is measured at the same time each day, to decrease day-to-day variation. The rats are constrained in dark chambers on a pre-heated platform to increase blood flow to the tail. A total of three to five measurements are averaged for each animal.

Statistics—The number of rats for each experiment (n=7) is based upon previous experience, where an n of 7 rats per group was sufficient to determine significance (80% power to detect alpha of 0.05 with a standard deviation of 10 and a difference of 15). Visual comparisons of immunocytochemical analyses are made by two individuals blinded to the identity of the samples. Statistical significance of differences is evaluated by ANOVA with p values corrected by Dunnett's post test, using the statistics package Instat (GraphPad). The criterion for statistical significance is $p<0.05$.

Example 3

Pilot Group Study

The safety, tolerability, and effectiveness of exo-S-mecamylamine as augmentation therapy in patients with refractory hypertension can be assessed in a double-blind, randomized, placebo-controlled, sequential group pilot study. Eighteen to sixty-five year-old male or female patient subjects will be taking three or more concomitant antihypertensive agents, including a diuretic and either an angiotensin converting enzyme inhibitor (ACEI or ACE inhibitor), an angiotensin receptor blocker (ARB, or AT2 receptor inhibitor), or a renin antagonist (RA)). Alpha-adrenergic blockers, beta-adrenergic blockers, hydralazine, clonidine, guanethidine, guanadrel, and rauwolfia alkaloids will be excluded; all other antihypertensive agents will be allowed. Inadequate blood pressure (BP) control is defined as systolic BP (SBP) >140 mmHg and a diastolic BP (DBP)>90 mmHg. Such studies can assess the safety and tolerability of exo-S-mecamylamine in patients with refractory hypertension; and 2) obtain preliminary dose-response estimates Exo-S-mecamylamine will be administered as the hydrochloride salt in doses of 1 mg, 2 mg, 4 mg and 8 mg (two×4 mg capsules) (free base equivalents) and matching placebo. The mode of administration will be oral.

Twelve subjects will be enrolled to ensure ten completers. The subjects with refractory hypertension (on three concomitant agents with SBP>140 mm Hg and a DBP>90 mm Hg) will be randomized in a double-blind fashion to receive single escalating doses of study medication in-clinic: on Day 1 (1 mg), Day 8 (2 mg), Day 15 (4 mg) and Day 22 (8 mg). On each of these 4 days, 10 subjects will receive exo-S-mecamylamine, and 2 subjects will receive placebo; the randomization will ensure that different subjects receive placebo (n=2) on each occasion. Placebo treatments will be pooled across the 4 days of single-dose to produce an equivalent reference cohort (n=8) for each treatment dose (n=10). Following the single-dose administration of 8 mg in the clinic on Day 22, subjects will continue with two weeks (Days 23-35) of outpatient self-administration of exo-S-mecamylamine (4 mg BID; n=6), or matching placebo (BID; n=6). On Day 36, subjects will return for a final in-clinic dose of either exo-S-mecamylamine (4 mg, n=6) or placebo (n=6). There will be a 1-week follow-up period at the end of the treatment period.

Subjects will have a documented record (at least 2 months) of refractory hypertension despite using 3 or more concomitant antihypertensive agents, including a diuretic and either an ACEI, ARB, or RA. On Days 1, 8, 15, 22 and 36, patients will have 3 separate manual BP determinations collected in a seated position (separated by 2 minute intervals) and 1 orthostatic blood pressure determination prior to dosing. Following dosing, 3 manual seated BP measurements will be obtained in an identical fashion, at 30 minutes post-dose and at 1, 2, 3, 4, 5, 6, 7, and 8 h post-dose. For each set of 3 BP measurements, a mean BP will be calculated. In addition, a pulse-wave scanner will be used to determine parasympathetic and sympathetic tone for each subject at Day 1 (pre-dose) and at Day 36 (pre-dose).

Statistical Analysis

ANCOVA (mean of the 3 seated determinations). All BP evaluations cited below are the means of 3 successive BP measurements. Mean difference between exo-S-mecamylamine and placebo in change at 3 h from baseline SBP by treatment. Baseline BP is defined for each clinic visit on Day 1, Day 8, Day 15 and Day 22 as the pre-dose BR Baseline BP for Day 36 is defined as the pre-dose BP on Day 22.

Key Secondary Differences (as Above):

1) Difference between exo-S-mecamylamine and placebo in change at 3 h from baseline DBP;

2) Time-matched differences in mean SBP and mean DBP for exo-S-mecamylamine compared to placebo; and 3) Dose vs. effect regression analysis for change from baseline SBP and baseline DBP.

Secondaries (all are Comparing Mean Exo-S-Mecamylamine Vs. Mean Placebo):

4) Mean Systolic Blood Pressure Effect (MSBPE) [ΔArea Under Effect Curve (AUEC) from 0 to 8 h post-dose/8 hr];

5) Mean Diastolic Blood Pressure Effect (MDBPE) [ΔAUEC from 0 to 8 h post-dose/8 hr];

6) Proportion of responders with reduction of SBP>/=10 mm Hg;

7) Proportion of responders with reduction of DBP>/=5 mm Hg;

8) Proportion of responders with reduction of SBP>/=5 mm Hg;

9) Proportion of responders with reduction of DBP>/=2.5 mm Hg; and

10) Change in parasympathetic and sympathetic tone, Day 36 compared to Day 1.

Post hoc tests will be conducted to explain the basis for any differences found on ANOVA.

Efficacy Analysis

The primary efficacy analysis will be performed using the primary efficacy endpoint for the Intent-to-Treat (ITT) population and Per Protocol (PP) population. To account for missing data during a clinic visit in the ITT population, the last-observation-carried-forward (LOCF) method will be used, i.e. the last available on-therapy observation for a subject during a clinic visit will be used to estimate subsequent missing data points in that clinic visit. Missing data will not be imputed between clinic visits.

Safety Analysis

All safety analyses will be performed for the Safety Population (i.e., ITT population plus any drop-outs). Adverse events will be coded by system organ class and preferred term using Medical Dictionary for Regulatory Activities (MedDRA). Treatment emergent adverse events (TEAE) will be tabulated and summarized by presenting the incidence (number and percentage of patients) in each treatment group. Incidence of orthostatic hypotension will be evaluated by dose. ECGs will be evaluated by subject and by dose. Lab abnormalities will be evaluated on a subject-by-subject basis.

Safety Outcome Measures:

Inspection of treatment-emergent adverse events; clinical measurements of orthostatic BP; inspection of electrocardiography (ECG) tracings; and laboratory measures of blood chemistry, hematology, liver function tests, lipid panel, and urinalysis.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

What is claimed is:

1. A combination comprising:
   a) at least one form of mecamylamine; and
   b) an ACE inhibitor, an AT2 receptor inhibitor, a renin inhibitor, a calcium channel blocker, or a combination thereof, wherein the combination provides for a decreased therapeutically effective amount of each component as individually administered.

2. A combination comprising:
   a) at least one form of mecamylamine; and
   b) an ACE inhibitor, an AT2 receptor inhibitor, a renin inhibitor, a calcium channel blocker, or a combination thereof, wherein the mecamylamine is exo-S-mecamylamine.

3. A combination comprising:
   a) at least one form of mecamylamine; and
   b) an ACE inhibitor, an AT2 receptor inhibitor, a renin inhibitor, a calcium channel blocker, or a combination thereof, wherein the AT2 receptor inhibitor is losartan.

4. A method for treating or inhibiting the onset of hypertension or refractory hypertension comprising administering:

a) at least one form of mecamylamine; and
b) at least one ACE inhibitor, AT2 receptor inhibitor, a renin inhibitor, a calcium channel blocker, or a combination thereof, wherein the hypertension is angiotensin-induced hypertension.

5. A method for treating or inhibiting the onset of hypertension or refractory hypertension comprising administering:
a) at least one form of mecamylamine; and
b) at least one ACE inhibitor, AT2 receptor inhibitor, a renin inhibitor, a calcium channel blocker, or a combination thereof, wherein the administration further reduces one or more of cardiac hypertrophy or fibrosis.

6. A method for treating or inhibiting the onset of hypertension or refractory hypertension comprising administering:
a) at least one form of mecamylamine; and
b) at least one ACE inhibitor, AT2 receptor inhibitor, a renin inhibitor, a calcium channel blocker, or a combination thereof, wherein the at least one form of mecamylamine is exo-S-mecamylamine.

7. A method for treating or inhibiting the onset of hypertension or refractory hypertension comprising administering:
a) at least one form of mecamylamine; and
b) at least one ACE inhibitor, AT2 receptor inhibitor, a renin inhibitor, a calcium channel blocker, or a combination thereof, wherein the administration further prolongs the control of blood pressure at sustained dosage levels.

8. A method for treating or inhibiting the onset of hypertension or refractory hypertension comprising administering:
a) at least one form of mecamylamine; and
b) at least one ACE inhibitor, AT2 receptor inhibitor, a renin inhibitor, a calcium channel blocker, or a combination thereof, wherein the at least one form of mecamylamine and the at least one ACE inhibitor, AT2 receptor inhibitor, a renin inhibitor, a calcium channel blocker, or a combination thereof is administered concomitantly.

9. A method for treating or inhibiting the onset of hypertension or refractory hypertension comprising administering:
a) at least one form of mecamylamine; and
b) at least one ACE inhibitor, AT2 receptor inhibitor, a renin inhibitor, a calcium channel blocker, or a combination thereof, wherein the method further comprises diagnosing refractory hypertension by determining a subject's response upon administration.

10. A method for treating or inhibiting the onset of hypertension or refractory hypertension comprising administering:
a) at least one form of mecamylamine; and
b) at least one ACE inhibitor, AT2 receptor inhibitor, a renin inhibitor, a calcium channel blocker, or a combination thereof, wherein the AT2 inhibitor is losartan.

* * * * *